US006517844B1

(12) United States Patent
Brinton

(10) Patent No.: US 6,517,844 B1
(45) Date of Patent: Feb. 11, 2003

(54) COMPOSITIONS AND METHOD FOR IMMUNIZING POULTRY

(76) Inventor: Marshall K. Brinton, 333 Lake Ave. N., Spicer, MN (US) 56288

( * ) Notice: Subject to any disclaimer, the term of this patent is extended or adjusted under 35 U.S.C. 154(b) by 0 days.

(21) Appl. No.: 09/312,575

(22) Filed: May 14, 1999

(51) Int. Cl.⁷ .................. A61K 39/02; A61K 39/10; A61K 39/116; A61K 33/554; G01N 33/554
(52) U.S. Cl. .................. 424/240.1; 424/203.1; 424/234.1; 424/204.1; 424/253.1; 424/254.1; 435/732; 435/38; 435/41; 435/693; 930/200
(58) Field of Search .................. 424/92, 114, 184.1, 424/203.1, 240.1, 253.1, 254.1, 803, 816, 826, 234.1; 435/32, 71.3, 7.32, 38, 41, 69.3; 536/16.8; 930/200

(56) References Cited

U.S. PATENT DOCUMENTS

| | | | | | |
|---|---|---|---|---|---|
| 3,855,408 A | * | 12/1974 | Maheswaran | ................. | 424/92 |
| 4,169,886 A | * | 10/1979 | Hertman et al. | .............. | 424/92 |
| 4,279,893 A | | 7/1981 | Kreimer et al. | ................ | 424/89 |
| 4,423,035 A | * | 12/1983 | Strayer | ........................ | 424/92 |
| 4,746,613 A | * | 5/1988 | Wichmann | .................. | 435/253 |
| 5,536,496 A | * | 7/1996 | Frantz et al. | ............. | 424/236.1 |
| 5,576,003 A | * | 11/1996 | Storm et al. | ............. | 424/234.1 |

OTHER PUBLICATIONS

Rice, B.E., et al., "Campylobacter jejuni in broiler chickens: colonization and humoral immunity following oral vaccination and experiment infection", *Vaccine, 15(17/18)*, pp. 1922–1932, (1997).

Nakamura, T., et al., "Protective Effect of Oral Administration of Killed Haemophilus paragallinarum Serotype A on Chickens", *Avian Diseases, 38*, No. 2, 289–292, (Apr.–Jun. 1994).

* cited by examiner

*Primary Examiner*—Nita Minnifield
*Assistant Examiner*—Jana Hines
(74) *Attorney, Agent, or Firm*—Schwegman, Lundberg, Woessner & Kluth, P.A.

(57) ABSTRACT

The present invention is directed to vaccine compositions and methods for immunizing poultry. The vaccine compositions comprise inactivated bacterial organisms which can be administered to the poultry through oral intake of water.

15 Claims, No Drawings

COMPOSITIONS AND METHOD FOR IMMUNIZING POLUTRY

BACKGROUND OF THE INVENTION

The current economic pressure on agriculture to produce foods cheaper, results in labor saving animal husbandry techniques which leave large populations of poultry at risk of contracting communicable diseases, often more than one disease at a time. When this does occur, and a farm flock is infected with concurrent infections, the results are usually devastating in regard to lost animals and lost production performance. Currently utilized vaccine technology has not resulted in an effective means to control this risk of concurrent infections.

Modified live vaccines have the advantage of being able to be applied or administered in the drinking water. However, certain drawbacks do exist. First, live vaccines can cause clinical disease particularly when they are delivered to birds that are stressed from either environmental problems or concurrent infections. Second, the administration of live vaccines in drinking water requires that the birds be vaccinated in a relatively short period of time, usually 2 to 4 hours, because live vaccines can die in the drinking water system used to water the birds. Thus, this often results in a situation where all the birds in the barn are not receiving an immunizing dose of the vaccine because they may not be drinking enough water during the period of time that the vaccine is being delivered. Third, since certain live vaccines (e.g., bacterial antigens) are susceptible to antibiotics, the birds typically cannot have received any antibiotic for 3 to 5 days prior to, or after, vaccination. The problem this creates is exemplified by a producer who has just spent money to vaccinate a flock against a disease using a live vaccine, and the next day the birds are showing signs of a digestive infection which could be easily treated with antibiotics. Unfortunately, if the producer treats the birds with antibiotics, the immunizing effect of the vaccine is lost. In addition, most live vaccines must be refrigerated during storage and shipping.

Inactivated vaccines that are administered parentally have the advantage that they can be delivered while the birds are being treated with antibiotics. However, this approach also has significant drawbacks associated with it. First, the obvious expense that is associated with handling individual birds in the vaccination process results in multiplying the cost 2 to 3 times over a mass vaccination approach such as used in modified live vaccines. Second, when the birds are going through a stress period, either environmental in nature or due to a concurrent infectious disease, the handling required for injecting individual birds can result in significant exacerbation of the clinical problem. Third, the risks associated with accidental injection of the vaccines to the people administering them has long been known, with some people losing fingers from severe inflammatory responses. Generally, inactivated vaccines also require refrigeration to prevent the adjuvant system from going rancid or breaking down in some other fashion.

Therefore, there is a need for an effective poultry vaccine that can be safely administered to a population of birds without exacerbating a stressful situation into a clinical problem. There is also a need for a vaccine that can be administered with antibiotics without detrimental effect to the immune response to the vaccine antigen. There is a further need for clinically useful vaccines which do not require refrigeration during storage or transportation. These and other needs are addressed by the present invention.

SUMMARY OF THE INVENTION

The present invention is directed to vaccine compositions and methods for safe and effective immunization of large populations of animals, particularly birds, through their drinking water.

It will be noted that at several places throughout the present specification, guidance is provided through lists of examples. In each instance, the recited lists serve only as a representative group. It is not meant, however, that the lists are exclusive.

A vaccine composition according to the invention includes an inactivated bacterin and a preservative. In one embodiment, the bacterin is present in one gallon of the vaccine composition at a concentration permitting a spectrophotometric transmission reading of up 12% at 540 nanometer per 10,000 doses of the vaccine. The inactivated bacterin can be derived from *Escherichia Coli*, *Bordetella avium*, a combination of *Bordetella avium* and *Ornithobacterium rhinotrachaeale*, *Riemerella anatipestifer* and *Pasteurella multocida*. Other bacterins suitable for the invention will become apparent to one of skill in the art after reading the present patent disclosure.

The vaccine composition preferably also includes a preservative. In one embodiment, the preservative is methyl/propyl paraben. In addition, a vaccine composition of the invention can also include an antibiotic.

The invention also provides a method for immunizing poultry with a vaccine composition of the invention in the drinking water of poultry. The vaccine composition can be administered to provide a priming immunization or booster immunization to the birds.

DETAILED DESCRIPTION OF THE INVENTION

To be clinically useful, an immunization system should preferably be safe, simple to perform, cost effective and clinically effective in preventing the targeted disease. The present invention provides such an immunization system.

Oral tolerance is a theory which explains why animals do not usually develop immune responses to the food they eat. This theory fosters the notion that orally dosed antigens do not result in meaningful immune protection against an inactivated antigen that is orally administered. However, in contrast to the traditionally held notions regarding orally administered antigens, the present invention provides compositions and methods for the safe and effective administration of an inactivated vaccine through an oral administration route.

In general, the compositions of the invention can be administered to mass populations of animals through their drinking water, over a 12–24 hour period, with confidence that all animals are receiving an effective immunizing dose of the vaccine. The vaccines can be administered to young animals or adults as a primary immunizing agent, or as a booster immunizing agent as needed. Advantageously, the vaccine compositions of the invention do not require refrigeration and thus can be cost effectively stored with little concern regarding efficacy if not administered immediately upon opening.

In a preferred embodiment the methods of the invention are particularly advantageous for administration to poultry. As used herein, the term "poultry" includes chickens, turkeys, pheasant, geese, duck, etc. The methods are particularly advantageous for use with intensive management operations of mass populations of birds.

As used herein, the term "bacterin" refers to a suspension of killed or attenuated bacteria. A bacterin according to the invention can also include a component of the bacteria, for example, fragments or components isolated from the whole organism, specific antigens genetically engineered, etc. In most preferred embodiments, the bacterin is an inactivated whole organism. In addition, the term "toxoid" refers to a toxin produced by an organism. Typically, a bacterin of the invention will also contain the toxins produced by the organism. In fact, as described below, the invention provides methods for increasing the level of toxins in the bacterin for enhanced immunogenicity.

Examples of disease conditions which can effectively be controlled by the compositions and methods of the invention include respiratory diseases, gastrointestinal diseases, central nervous system disease, etc. Respiratory disease problems which can typically arise in confinement housing operations include mortality, morbidity, loss of performance (i.e., decreased rate of gain or feed conversion), and loss of wholesomeness due to chronic airsaculitis.

Typically, the infectious components of respiratory disease of turkeys include *Bordetella avium* (BART), primary or virulent serotypes of *Escherichia coli* (serotypes 01, 02, and 078), *Ornithobacterium rhinotracheale* (ORT), Newcastle Disease Virus, Avian Pneumo virus, and perhaps other not yet identified agents.

BART is a disease which has its most significant clinical affects if the birds are initially infected in the first few weeks of life. Early infection can result in denudation of the tracheal cilia which can exacerbate the pathogenicity of respiratory organisms because of the birds' inability to clear the infection from the respiratory tract. Primary *E. coli* can result in severe clinical disease by itself, but is much more severe when the birds are infected with BART. It has been hypothesized that a severe infection with toxigenic *E. coli* can result in direct damage to the heart muscles and develop a condition known as "flabby heart" or cardiac dilatation.

ORT causes the most severe clinical disease when the birds are first infected as young adults, seventeen to eighteen weeks of age. This disease can result in severe pulmonary inflammation which can interact with the primary *E. coli* and put more pressure on the heart muscles resulting in more severe cardiac dilatation.

Newcastle disease virus is not seen as a significant disease unless it is acting in concert or at the same time as another respiratory disease.

Pneumo virus is also viewed as not significantly pathogenic unless it interacts in birds with one or more of the other respiratory pathogens listed above.

Prior vaccine technology has not resulted in effective means of dealing with all these potential interactive respiratory diseases of confinement animals. The present invention is directed to addressing the problems with prior immunization systems through oral administration of an inactivated antigen. In addition, to being contrary to traditional oral tolerance theories, a significant hurdle in attempting to develop the present vaccine systems was the difficulty in measuring mucosal immune responses. That is, it was extremely difficult to evaluate specific oral antigen concentrations required to produce optimum mucosal immune response. The inventor has overcome this hurdle by using the lack of systemic immune response to evaluate the efficacy of the inactivated orally dosed bacterins disclosed herein. As described in the Examples, farms having a history of severe infectious disease problems and subsequent disease problems were studied to confirm the efficacy of the composition and methods of the invention.

In the case of BART, when orally dosing the presently disclosed inactivated BART bacterin, the flocks on the immunized farms were negative for BART using ELISA tests which measured circulating or systemic antibodies. Based on this information, turkeys vaccinated with the inactivated BART bacterin did not result in circulating or systemic antibodies. Thus, the BART bacterin was successful in preventing BART from becoming a systemic infection by blocking the disease at the surface or at the mucosal level. Because there is no convenient ELISA test for *E. coli*, the same antigenic concentration used for the BART bacterin was also used to develop an *E. coli* bacterin with similar clinical success.

Additional vaccine compositions of the invention include inactivated bacterins comprising *Reimerella anatipestifer*; a combination of *Bordetella avium* and *Ornithobacterium rhinotracheale*; and *Pasteurella multocida*. In view of the present disclosure, other vaccines within the scope and spirit of the invention will apparent to one skilled in the art.

The bacterins of the invention are prepared from bacterial cultures grown on a suitable culture media. Most media suitable for propagation of a particular organism are suitable for the invention. The bacterial cultures are screened to establish the purity of a particular organism and the organisms are inactivated. Methods of inactivation useful according to the invention, include, for example, formalin treatment, heat treatment, hypochlorite treatment, irradiation, and other methods known in the art. In a preferred embodiment, the organisms are inactivated with 0.3%–0.4% v/v formalin.

The antigenic content of a composition of the invention can be determined using most known methods for ensuring a particular antigenic concentration. In a preferred method, the antigenic content is measured using a spectrophotometer reading at a wavelength of 540 nanometer. In general, a suitable concentration of the antigen is about 1%–15%, preferably about 2%–10% transmission at 540 nanometer.

Preservatives may also be added to a vaccine composition. Most known preservatives are suitable. However, in a preferred embodiment, methyl/propyl paraben is used. The preservative can also include red food-grade dye. In one particularly preferred embodiment, the preservative comprises methyl/propyl paraben containing 1–2% red food dye. The preservative combination is preferably present in the vaccine composition at a concentration of about 1%–2% v/v.

Antibiotics can also be added to the vaccine composition. Suitable antibiotics include penicillins (e.g., penicillin, ampicillin, amoxicillin, etc.), cephalosporins, aminoglycosides (e.g., gentamycin, streptomycin, amakacin, etc.), sulfas, tetracyclines, etc. In some preferred embodiments a suitable, cost effective antibiotic system is penicillin and streptomycin.

The vaccine compositions are preferably bottled in an easy to use container having a sufficient number of dosages for the particular application. Generally screw top one gallon plastic bottles can be used. The compositions can be formulated to contain 5,000–30,000, typically about 10,000 to 20,000 doses per gallon. To provide an adequate dosage to a flock of about 20,000 birds, 1 gallon of a 20,000 dose container is mixed with the amount of water the birds would consume in 24 hours. Thus, the concentration of the vaccine composition in the water supply for younger birds (lower body weight) will be greater than that for birds of a higher body weight due to lower overall water consumption in younger birds.

In one embodiment, one gallon of a vaccine composition containing sufficient antigen at 9% transmission at 540 nm is administered to 10,000 birds over a 24 hour period every 3 to 7 days for the life of the bird. In another embodiment, a one gallon composition containing sufficient antigen at 3.5% transmission at 540 nm is administered to 20,000 birds over a 24 hour period every 3 to 7 days for the life of the bird.

According to the invention, the frequency that the birds are immunized with a vaccine composition of the invention can vary with the perceived challenge of a pathogenic organism. Thus, if the perceived level of challenge is high, the frequency of reimmunization is preferably increased.

EXAMPLES

The following Examples are provided to describe certain preferred compositions and methods of the invention. However, the scope of the invention should not be interpreted as being limited to the Examples provided.

Example 1

A. *Bordetella avium* Bacterin

The microorganism used for this bacterin was a strain of *Bordetella avium* ("BART") (gram negative rod, non-lactose fermenter) which was isolated from turkeys and diagnosed as virulent to turkeys. The organism was cultured and isolated from the tracheas of a turkey flock exhibiting respiratory distress. To ensure purity, the third passage of the organism on blood agar was collected and stored as the master seed stock. A single strain of the BART organism, identified as Pathotype 40, was used. The identity of the BART organism was reconfirmed prior to harvest of production cultures using known biochemical identification methods on blood agar and/or MacConkey agar.

1. Preparation of Production Culture

The seed cultures and production cultures were grown in tryptic soy broth containing 2% glycerol and 0.01% silicone anti-foaming agent (other suitable media are known and can be used). Production cultures consisted of 7 liters of the media which was sterilized by steam/pressure sterilization prior to use. Other methods for sterilization which are within the skill in the art can be used. The cultures were grown in 9 liter glass serum bottles. Each bottle was equipped with an inoculation hose to allow inoculation of the seed culture into the production culture. Each vessel was also equipped with a hose/dispersion stone system to allow gas dispersion within the culture. The seed cultures can be stored using suitable methods, preferably ultra-cold (i.e., less than −70° C.) or lyophilized.

The Bordetella seed stock was stored in an appropriate freezing medium such as 2× sterile skim milk in liquid nitrogen (or other ultra-low temperature freezer). Alternatively, the seed stock may also be lyophilized. The seed stock was removed from storage and thawed, or rehydrated, at room temperature and aseptically transferred to one or more vessels containing seed media. Seed suspensions were initially placed in a 35 to 38° C. incubator for 18 to 48 hours. However, if the seed culture is adequately concentrated, (showing moderate to dense concentration) it may be directly transferred to the production media. Thus, prior to inoculation into the production media, the seed media suspension preferably demonstrates satisfactory concentration and/or growth. The seed stock for the production culture can be inoculated into multiple 100 ml glass, round, screw cap bottles containing 30 to 70 ml media or one 3 to 9 liter vessel containing 1.7 to 7 liters tryptic soy broth.

The production culture media was pre-warmed to 35 to 38° C. prior to inoculation. Prior to inoculation, each production vessel was connected to the desired gas/aeration source. Preferred gas sources can be either compressed oxygen, or compressed air. Preferably, a sterile 0.2 micron filter, or other acceptable filtering system ensuring gas sterility, was aseptically placed between the gas source and vessel gas inlet hose.

To inoculate the production cultures, sterile technique was used, preferably within a biological safety cabinet. 30 to 70 ml of seed culture was drawn into a sterile syringe (or other suitable apparatus) and aseptically injected/introduced into 7 liters of the production culture media. The seed cultures were incubated for 18 to 48 hours at 35 to 38° C. and the production cultures were incubated for 32 hours (24 to 48) at 35 to 38° C.

Compressed air or oxygen was dispersed throughout the production culture media to create a simmering appearance of the media during the first 8 hours of incubation. Gas flow was increased to give the media the appearance of a low boil from 8 to 24 hours post inoculation. At 18 to 30 hours post inoculation, 50 ml of 1M NaOH was introduced into each production vessel. Gas flow was increased following NaOH addition to give the media the appearance of a rolling boil. Production cultures were allowed to incubate a minimum of an additional 6 to 8 hours prior to inactivation. Preferably, the time from inoculation to harvesting is in the range of 28–36 hours.

The production cultures preferably exhibit dense to extremely dense bacterial growth at the time of inactivation. The production cultures were inactivated with 0.3% to 0.4% v/v formaldehyde following the incubation period.

It will be appreciated that in each of the vaccine compositions described, the bacteria were "shocked" with NaOH during the log phase of growth to enhance the levels of toxin produced.

2. Harvesting Production Cultures

After inactivation, with 0.3% to 0.4% v/v formalin, at about 28 to 36 hours post inoculation, the production cultures were allowed to incubate at 35 to 38° C. for a minimum of 18 hours. Cultures determined to be pure were pooled in large sterile storage vessels and stored at 10 to 35° C. until further processed. Yield was considered satisfactory upon a spectrophotometer reading of less than or equal to 5% transmission at 540 nm wavelength.

3. Preparation of Product

Following vigorous stirring of the harvest material, a sample was collected for standardization. Using a spectrophotometer set at wavelength 540, the % transmission of the sample was determined. Transmissions reading less than 3.5% were standardized to equal 3.5% by adding distilled water. Transmissions reading greater than 3.5% were reworked with material reading less than 3.5% to achieve a concentration of 3.5% or less. Prior to standardization, the harvest material was pooled in a sterile mixing vessel and impelled for a minimum of one hour.

A formalin preservative was added to a final product formalin concentration of 0.05–0.2% as measured by the Residual Free Formalin Test. A stabilizer comprising methyl/propyl paraben containing 1–2% red food-grade dye was also added to the final product to a concentration of 1% to 2% v/v. Penicillin was added to the final product to contain 189.250 IU per gallon. Streptomycin can also be added to the final product to contain 250 to 500 mg streptomycin per gallon.

The average serial volume consisted of about 400 gallons and the maximum consisted of about 600 gallons. One gallon of the final product +/−5% can be dispensed in plastic gallon containers. The containers can be filled using a pre-chemically sterilized multiple spigot siphon fill/pump system adjusted to deliver one gallon per container. Containers can be hand sealed with screw-cap closures. Each gallon contains approximately 20,000 doses.

The product was used in turkeys, but can also be used in other poultry determined to be at risk of infection. One gallon was administered in the amount of drinking water which would be consumed by 20,000 poults in a 24 hour period.

B. Clinical Trial

A farm with a history of a significant *Bordetella avium* infection in the brooder barn had experienced an average 15% mortality rate by the time the birds were 5 weeks old. This mortality rate was seen in the previous 3 flocks through the farm. With the worsening condition of each subsequent flock, the down time between flocks had shortened to only 4 days. The brooder barn was tested to evaluate the cleaning and disinfecting program used and found to be unsatisfactory. The farm therefore was at considerable risk of experiencing the same if not a worse mortality rate in the next flock.

The farm began orally administering the BART bacterin, described above, when the birds of the flock were 2 weeks of age. Subsequent oral doses were administered every 4 days thorough the first 5 weeks of age. The flock was moved from the brooder at 5 weeks of age with a mortality rate of 2.3%. Subsequent flocks vaccinated with the Bordetella toxoid/bacterin revealed that the orally dosed toxoid/bacterin did not result in any measurable humoral antibody titers. The lack of seroconversion, following the administration of the oral toxoid, was used to determine the level of control against Bordetella infection that was achieved using the toxoid.

Example 2

A. *Escherichia Coli* Bacterin

The microorganism used for this bacterin are three types of *Escherichia coli*, (*E. coli*), types 01, 02, and 078. All are gram negative rods. Types 01 and 078 are lactose fermenters and type 02 is a non-lactose fermenter. The organisms were cultured and isolated from the liver of turkey flocks exhibiting respiratory and/or enteric disease. The third passage of the organisms on blood agar plates was stored as the master seed stock.

Each of the types were isolated from morbid turkeys and each type diagnosed as virulent to turkeys. The three serotypes of *E. coli* comprise the antigenic portion of the bacterin and each serotype comprises one third of the antigenic portion of the bacterin. The identity of the *E. coli* organism was reconfirmed prior to harvesting of production cultures using known biochemical identification methods on blood agar and/or MacConkey agar. Production culture purity was determined prior to harvest using the same biochemical identification methods.

1. Preparation of Production Culture

The seed cultures and production cultures were grown in tryptic soy broth containing 2% glycerol and 0.01% silicone anti-foaming agent (other suitable media are know and can be used). Production cultures consisted of 7 liters of the media and was sterilized by steam/pressure sterilization prior to use.

Other methods for sterilization which are within the skill in the art can be used. The cultures were grown in 9 liter glass serum bottles. Each bottle was equipped with an inoculation hose to allow inoculation of the seed culture into the production culture. Each vessel was also equipped with a hose/dispersion stone system to allow gas dispersion within the culture. The seed culture can be stored ultra-cold or lyophilized.

The *E. coli* seed stock was stored in an appropriate freezing medium such as 2× sterile skim milk, and stored in liquid nitrogen (or other ultra-low temperature freezer). Alternatively, the seed stock may also be lyophilized. The seed was removed from storage and thawed, or rehydrated, at room temperature and aseptically transferred to one or more vessels containing seed media. Seed suspensions were initially placed in a 35–38 degree C. incubator for 18 to 48 hours. However, if the seed culture is adequately concentrated (showing moderate to dense concentration), it may be directly transferred to the production media. Thus, prior to inoculation into production media, the seed media suspension preferably demonstrates satisfactory concentration and/or growth. The seed stock for culture can be inoculated into 100 ml glass, round screw cap bottles containing 30 to 70 ml tryptic soy broth, or one 3 to 9 liter vessel containing 1.7 to 7 liters tryptic soy broth.

The production culture media was pre-warmed to 35 to 38° C. prior to inoculation. Prior to inoculating, each production vessel was connected to the desired gas/aeration source. Gas sources can be either compressed oxygen, or compressed air. Preferably, a sterile 0.2 micron filter, or other acceptable filtering system ensuring gas sterility, was aseptically placed between gas source and vessel gas inlet hose.

To inoculate the production cultures, sterile technique, preferably within a biological safety cabinet and 30 to 70 ml seed culture was drawn into a sterile syringe (or other suitable apparatus). The seed culture was then aseptically injected/introduced into 7 liters of the production culture media. The seed cultures were incubated for 18 to 48 hours at 35 to 38° C. and the production cultures were incubated for 32 hours (24 to 48) at 35 to 38° C. Compressed air or oxygen was dispersed throughout the media to create a simmering appearance of the media during the first 8 hours of incubation. Gas flow was increased to give the media the appearance of a low boil from 8 to 24 hours post inoculation. At 18 to 30 hours post inoculation, 50 ml of 1M NaOH was introduced into each production vessel. Gas flow was increased following NaOH addition to give the media the appearance of a rolling boil. Production cultures were allowed to incubate a minimum of an additional 6 to 8 hours prior to inactivation. Preferably, the time from production to harvesting is in the range of 28–36 hours.

The production cultures preferably exhibit dense to extremely dense bacterial growth at the time of inactivation. The production cultures were inactivated with 0.3% to 0.4% v/v formalin following the incubation period.

2. Harvesting Production Cultures

After inactivation, using 0.3% to 0.4% v/v formalin, at about 28–36 hours post inoculation, the production cultures were allowed to incubate at 35–38° C. for a minimum of 18 hours. Cultures determined to be pure were then pooled in large sterile storage vessels and stored at 10–35° C. until further processed. Yield was considered satisfactory upon a spectrophotometer reading of less than or equal to 5% transmission at 540 nm wavelength.

3. Preparation of Product

Following vigorous stirring of the harvest material, a sample was collected for standardization. Using a spectrophotometer set a wavelength 540, the % transmission of the sample was determined. Transmissions reading less than 2% were standardized to equal 2% by adding distilled water to the harvest material. Transmissions reading greater than 2% were reworked with material reading less than 2% to achieve a concentration of 2% or less. Prior to standardization, the harvest material was pooled in a sterile mixing vessel and impelled for a minimum of one hour.

A formalin preservative was added to a final product formalin concentration of 0.05–0.2% formalin as measured by the Residual Free Formalin Test. A stabilizer comprising methyl/propyl paraben containing 1–2% red food-grade dye was also added to the final product to a concentration of 1% to 2% v/v. Penicillin was added to the final product to contain 189.250 IU per gallon. Streptomycin can also be added to the final product to contain 250 to 500 mg streptomycin per gallon.

Prior to dispensing, the final solution was mixed for a minimum of 15 minutes following addition of all components.

The average volume consisted of about 400 gallons and the maximum consisted of 600 gallons.

One gallon of final product +/−5% shall be dispensed in plastic gallon containers. The containers can be filled using a pre-chemically sterilized multiple spigot siphon fill/pump system adjusted to deliver one gallon per container. Containers can be hand sealed with screw-cap closures Each gallon contains approximately 20,000 doses.

This product can be used for most poultry. One gallon was administered in the drinking water consumed by 20,000 birds over a 24 hour period.

4. Clinical Trials

A farm, which raises commercial geese, began orally administering the *E. coli* bacterin described above at one week of age and delivered the toxoid to the geese once a week for the first 8 weeks of age.

Two years prior to using the bacterin, the farm raised 104,000 geese and had a total of 65 cases for submissions to our lab to determine the nature of the unacceptable morbidity or mortality during the production cycle. Out of these 65 cases, 25 were diagnosed as pure *E. coli* infections based on microbiological testing.

One year prior to using the toxoid, the farm raised 134,000 geese and submitted 51 cases to our lab to determine the cause of the unacceptable morbidity or mortality. Of these 51 submissions, 28 were diagnosed as pure *E. coli* infections based on the same microbiological testing as the previous year.

The year the farm used the bacterin, the farm raised 144,000 geese. In this year the farm submitted just 23 cases to determine the cause of unacceptable mortality or morbidity. Out of these 23 submissions, only 2 were diagnosed as pure *E. coli* infections based on the same microbiological tests as the previous 2 years.

As can be seen from the above, use of the *E. coli* bacterin resulted in an approximate 10 fold reduction in clinical *E. coli* infections with no change in the frequency of other clinically significantly problems.

Example 3

A. *Riemerella anatipestifer* Bacterin

The microorganism used for this bacterin was a strain of *Riemerella anatipestifer* (gram negative rod) which was isolated from turkeys and diagnosed as virulent to turkeys. The organism was cultured and isolated from a turkey flock exhibiting infection. The third passage of the organism on blood agar was stored as a master seed stock. A single strain of the organism, identified as *Riemerella anatipestifer* PA98-1383, was used. 100% of the antigen fraction of this bacterin is *Riemerella anatipestifer* PA98-1283.

The identity of the *Riemerella anatipestifer* organism was reconfirmed prior to harvest of the production culture using known biochemical identification methods on blood agar. Production culture purity was determined prior to harvest using methods discussed above.

1. Preparation of Production Culture

The seed cultures and production cultures were grown in tryptic soy broth containing 2% glycerol and 0.01% silicone anti-foaming agent (other adequate media formulations are known and can be used). Production cultures consisted of 7 liters of the media and was sterilized by steam/pressure sterilization prior to use. Other methods for sterilization which are within the skill in the art can be used.

The cultures were grown in 9 liter glass serum bottles. Each bottle was equipped with an inoculation hose to allow inoculation of the seed culture into the production culture. Each vessel was also equipped with a hose/dispersion stone system to allow gas dispersion within the culture. The seed cultures can be stored ultra-cold or lyophilized.

The *Riemerella anatipestifer* seed stock was stored in an appropriate freezing medium such as 2× sterile skim milk in liquid nitrogen (or other ultra-low temperature freezer). Alternatively, the seed stock may also be lyophilized. The seed stock was removed from storage and thawed, or rehydrated, at room temperature and aseptically transferred to one or more vessels containing seed media. Seed suspensions were initially placed in a 35–38 degree C. incubator for 18 to 48 hours. However, if the culture is adequately concentrated (showing moderate to dense concentration), it may be directly transferred to the production media. Thus, prior to inoculation into the production media, the seed media suspension preferably demonstrates satisfactory concentration and/or growth. The seed stock for culture can be inoculated into multiple 100 ml glass, round screw cap bottles (or other appropriate vessels), containing 30–70 ml media or one 3 to 9 liter vessel containing 1.7 to 7 liters of production broth.

The production culture media was pre-warmed to 35 to 38° C. prior to inoculation. Prior to inoculating, each production vessel shall be connected to the desired gas/aeration source. Gas sources can be either compressed oxygen, or compressed air. Preferably, a sterile 0.2 micron filter, or other acceptable filtering system ensuring gas sterility, was aseptically placed between the gas source and vessel gas inlet hose.

To inoculate the production cultures, a sterile technique was used, preferably within a biological safety cabinet, and 30 to 70 ml seed culture was drawn into a sterile syringe (or other suitable apparatus). The seed culture was then aseptically injected/introduced into 7 liters of the production culture media The seed cultures were incubated for 18 to 48 hours at 35–38° C. and the production cultures were incubated for 32 hours (24 to 48) at 35 to 38° C.

Compressed air or oxygen was dispersed throughout the production culture media to create a low boiling appearance of the media during the first 8 hours of incubation. Gas flow was increased to give the media the appearance of a rolling boil from 8 to 24 hours post inoculation. At 18 to 30 hours post inoculation, 50 ml of 1M NaOH was introduced into each production vessel. Gas flow was increased following NaOH addition to give media the appearance of a high rolling boil. Production cultures were allowed to incubate a minimum of an additional 6 to 8 hours prior to inactivation. Preferably, the time from inoculation to harvest is 28–36 hours. Minimum time shall be 28 hours. Maximum time shall be 36 hours.

The production cultures preferably exhibit dense to extremely dense bacterial growth at time of inactivation. The production cultures were inactivated with 0.3% to 0.4% v/v formaldehyde following incubation period.

2. Harvesting Production Cultures

After inactivation, using 0.3% to 0.4% v/v formalin, at about 28–36 hours post inoculation, the production cultures were allowed to incubate at 35–38° C. for a minimum of 18 hours. Cultures determined to be pure were then pooled in large sterile storage vessels and stored at 10–35° C. until further processed. Yield was considered satisfactory.

3. Preparation of Product

Following vigorous stirring of harvest material, a sample was collected for standardization. Using a spectrophotometer set a wavelength 540, the % transmission of the sample was determined. Transmissions reading less than 3.5% shall be standardized to equal 3.5% by adding distilled water to the harvest material. Transmissions reading greater than 3.5% were reworked with material reading less than 3.5% to achieve a concentration of 3.5% or less. Prior to standardization, harvest material was pooled in a sterile vessel and impelled for a minimum of one hour.

A formalin preservative was added to a final formalin concentration of 0.05–0.2% as measured by the Residual Free Formalin Test. A stabilizer comprising methyl/propyl paraben containing 1–2% red food-grade dye was also added to the final product to a concentration of 1% to 2% v/v. Penicillin was added to the final product to contain 189.250 IU per gallon. Streptomycin was added to the final product to contain 250 to 500 mg streptomycin per gallon.

The average serial volume consisted of 400 gallons and the maximum serial volume consisted of 600 gallons. One gallon of the final product +/−5% can be dispensed in plastic gallon containers. The containers can be filled using a pre-chemically sterilized multiple spigot siphon fill/pump system adjusted to deliver one gallon per container. Containers cab be hand sealed with screw-cap closures. Each gallon contains approximately 20,0000 does.

This product was used in turkeys but can also be used for most other poultry at risk of contracting *R. anatipestifer*, particularly ducks. One gallon of the composition was administered in the amount of drinking water which would be consumed by 20,000 poults over a 24 hour period.

B. Clinical Trial

A farm that raises male turkeys was diagnosed as developing a farm infection consisting of *Riemerella anatipestifer* serotype 5. Four consecutive flocks placed on the farm broke with the infection, which resulted in high mortality and morbidity. The isolate was used to develop an inactivated bacterin, as described above, that was delivered to the fourth and subsequent flocks placed on the farm, starting at 2 weeks of age, and delivered every 4 to 5 days until the birds were 16 weeks old. It should be noted that the first flock to be vaccinated with the toxoid was 4 weeks old when the vaccine was started. This flock was in the process of breaking with the infection the day the vaccine was started. The vaccine was able to curb the infection and halt its progression in this, the first flock that was vaccinated. Since the first flock vaccinated (the fourth flock to be infected with *R. anatipestifer*), no other flocks have had clinical disease and/or have been diagnosed as infected with the organism.

Example 4

Since 1996 our lab has been identifying turkey flocks infected with Pneumovirus, *Ornithobacterium rhinotracheale*, *Bordetella avium*, and Newcastle disease virus. These flocks can experience severe mortality, in excess of 50%, and can experience severe condemnation rates at the plant. We have produced an inactivated bacterin consisting of *Bordetella avium*, and *Ornithobacterium rhinotracheale*, as described below. The bacterin can be delivered once a week at a rate of 1 gallon per 750 gallons of drinking water. The bacterin has been shown to significantly reduce the effects of the concurrent infections that can interact with the Pneumovirus.

A. *Bordetella avium-Ornithobacterium rhinotracheale* Bacterin

The microorganisms used for this bacterin was a strain of *Bordetella avium* ("BART")(gram negative rod, non-lactose fermenter) and a strain of *Ornithobacterium rhinotracheale* (gram negative rod) which were isolated from turkeys and diagnosed as virulent to turkeys. The BART used in this bacterin was cultured and isolated from the tracheas of a turkey flock exhibiting respiratory disease. The third passage of the organism on blood agar was stored as a master seed stock. The *Ornithobacterium rhinotracheale* ("ORT") was also cultured and isolated from tracheas of a turkey flock exhibiting respiratory disease. The seventh passage of the organism through tryptic soy broth was stored as a master seed stock. A single strain of each organism was used in this bacterin. Each of the organisms comprise 50% of the antigen fraction in this bacterin.

The identity of the organisms was reconfirmed prior to harvest of production cultures using known biochemical methods on blood agar and/or MacConkey agar. Production Culture purity was determined prior to harvest using the same biochemical identification methods discussed above.

Although the present Example is directed to a BART/ORT combination vaccine, it will be appreciated that a vaccine composition comprising only ORT can be prepared according to the disclosed methods.

1. Preparation of Culture

The seed cultures and production cultures were grown in tryptic soy broth containing 2% glycerol and 0.01% silicone anti-foaming agent (or other suitable media formulation) for BART, For ORT, the culture media consisted of tryptic soy broth containing 0.4% silicone anti-foaming agent and 10 grams of lactose per liter of media. Production cultures consisted of 7 liters of the media and was sterilized by steam/pressure sterilization prior to use.

The cultures were grown in 9 liter glass serum bottles. Each bottle was equipped with inoculation hoses to allow inoculation of the seed culture into the production culture. Each vessel was also equipped with a hose/dispersion stone system to allow gas dispersion within the culture. The seed cultures can be stored as described for the previous organisms.

The seed stock of each organism was stored in an appropriate freezing medium such as 2× sterile skim milk in liquid nitrogen (or other ultra-low temperature freezer). Alternatively, the seed stock may also be lyophilized. The seed stock was removed from storage and thawed, or rehydrated, at room temperature and aseptically transferred to one or more vessels containing seed media. Seed suspensions were then placed in a 35–38 degree C. incubator for 18 to 48 hours. However, if the seed culture was adequately concentrated, it may be directly transferred to production media. Thus, prior to inoculation into the production media, the seed media suspension preferably demonstrates satisfactory concentration and/or growth. The seed stock for culture can be inoculated into multiple 100 ml glass, round screw cap bottles containing 30 to 70 ml media or a 3 to 9 liter vessel containing 1.7 to 7 liters tryptic soy broth.

The production culture media was pre-warmed to 35 to 38° C. prior to inoculation. Prior to inoculating, each production vessel was connected to the desired gas/aeration source. Gas sources shall be either compressed oxygen, or compressed air. A sterile 0.2 micron filter, or other acceptable filtering system ensuring gas sterility was aseptically placed between the gas source and the vessel gas inlet hose.

To inoculate the production cultures, sterile technique was used, preferably within a biological safety cabinet, 30 to 70 ml seed culture was drawn into a sterile syringe (or other suitable apparatus). The seed culture was then aseptically injected/introduced into the 7 liter production culture.

The seed cultures were incubated for 18 to 48 hours at 35–38° C. and the production cultures were incubated 24 to 32 hours (24 to 48) at 35 to 38° C. BART production cultures had compressed air or oxygen dispersed throughout the media to create a simmering appearance of the media during the first 8 hours of incubation. Gas flow was increased to give the media the appearance of a low boil from 8 to 24 hours post inoculation. At 18 to 30 hours post inoculation, 50 ml of 1M NaOH was introduced into each production vessel. Gas flow was increased following NaOH addition to give media the appearance of a rolling boil. Production cultures were allowed to incubate a minimum of an additional 6 to 8 hours prior to inactivation.

ORT production cultures had compressed air dispersed throughout the media to create the appearance of a low boil for the first 16 to 18 hours post inoculation. At 16 to 18 hours post inoculation, 1M NaOH was introduced into each production vessel. Following addition of NaOH, gas flow was increased to give the media the appearance of a rolling boil, causing visible bubbling throughout the top ⅓ of the media. The production cultures preferably exhibit dense to extremely dense bacterial growth at the time of inactivation.

The production cultures were inactivated with 0.3% to 0.4% v/v formaldehyde following the incubation period. Preferably, the time from inoculation to harvesting is in the range of 22–36 hours. Minimum time shall be 22 hours. Maximum time shall be 36 hours.

2. Harvesting Production Cultures

After inactivation with 0.3% to 0.4% v/v formalin, at about 28–36 hours post inoculation, the production cultures were allowed to incubate at 35–38° C. for a minimum of 18 hours. Cultures determined to be pure were then pooled in large sterile storage vessels and stored at 10–35° C. until further processed. Yield was considered satisfactory upon a spectrophotometer reading of less than or equal to 10% transmission at 540 nm wavelength.

3. Preparation of Product

Following vigorous stirring of the harvest material, a sample was collected for standardization. Using a spectrophotometer set at wavelength 540, the % transmission of the sample was determined. Transmissions reading less than 9% were standardized to equal 9% by adding distilled water to the harvest material. Transmissions reading greater than 9% were reworked with material reading less than 9% to achieve a concentration of 9% or less.

A formalin preservative was added to a final product concentration of 0.05–0.2% as measured by the Residual Free Formalin Test. A stabilizer comprising methyl/propyl paraben containing 1–2% red food-grade dye was also added to a final concentration of 1 to 2% v/v. Penicillin was added to the final product to contain 189.250 IU per gallon. Streptomycin was added to the final product to contain 250 to 500 mg streptomycin per gallon.

The average serial volume consisted of 400 gallons and the maximum consisted of 600 gallons. One gallon of final product +/−5% can be dispensed in plastic gallon containers. The containers can be filled using a pre-chemically sterilized multiple spigot siphon fill/pump system adjusted to deliver one gallon per container. Containers can be hand sealed with screw-cap closures. Each gallon contains approximately 20,000 doses.

This product was used in turkeys but also can be used in other birds at risk of infection by ORT and/or BART. One gallon can be administered in the amount of drinking water which would be consumed by 10,000 poults over a 24 hour period. However, in preferred methods the vaccine composition is administered at a constant concentration of one gallon per 750 gallons of water per 24 hour drinking period. Thus, as the amount of water consumed increases with increasing bird age, the amount of antigen received also increases.

Example 5

The methods for preparing the foregoing bacterins was also used to prepare *Pasteurella multocida*, as described below. This vaccine composition can be orally administered to poultry at a concentration of one gallon of drinking water consumed over a 24 hour period by 10,000 birds.

A. *Pasteurella multocidal* Bacterin

The microorganisms used in this bacterin are strains of *Pasteurella multocida* (gram negative rod) which were isolated from and diagnosed as virulent to poultry. The organism used in this bacterin was cultured and isolated from flock(s) exhibiting respiratory disease. A single or multiple strains can be used.

Each strain used can be incorporated into this bacterin in equal amounts. The identity of the organisms used was reconfirmed prior to harvest of production cultures using known biochemical identification methods. Identification was performed on blood agar plates. Production culture purity was determined prior to harvest of production cultures using the same biochemical methods discussed above.

1. Preparation of Production Cultures

The seed cultures and production cultures were grown in tryptic soy broth containing 2% glycerol and 0.01% silicone anti-foaming agent (or other suitable media formulation). Production cultures consisted of 7 liters of the media and was sterilized by steam/pressure sterilization prior to use. Other methods for sterilization which are known in the art can also be used.

The cultures shall be grown in 9 liter glass serum bottles. Each bottle/vessel was equipped with inoculation hoses to allow inoculation of the seed culture into the production culture. Each vessel was also equipped with a hose/dispersion stone system to allow gas dispersion within the culture. The seed cultures can be stored ultra-cold or lyophilized.

Pasteurella seed stock was stored in an appropriate freezing medium such as 2× sterile skim milk in liquid nitrogen. Alternatively, the seed stock may be lyophilized. The Seed stock was removed from storage and thawed, or rehydrated, at room temperature and aseptically transferred to one or more vessels containing seed media. Seed suspensions were initially placed in a 35–38 degree C. incubator for 18 to 48 hours. However, if the seed culture is adequately concentrated (shown in moderate to dense concentration), it may be directly transferred to the production media. Thus, prior to inoculation into the production media, the seed media suspension preferably demonstrates satisfactory concentration and/or growth. 100 ml glass, round screw cap bottles containing 30 to 70 ml media or one 3 to 9 liter vessel containing 1.7 to 7 liters tryptic soy broth.

The production media was pre-warmed to 35 to 38° C. prior to inoculation. Prior to inoculating, each production vessel was connected to the desired gas/aeration source. Gas sources are preferably either compressed oxygen, or compressed air. Preferably, a sterile 0.2 micron filter, or other acceptable filtering system ensuring gas sterility, was aseptically placed between the gas source and vessel gas inlet hose.

To inoculate the production cultures, sterile technique was used, preferably within a biological safety cabinet, and 30 to 70 ml seed culture was drawn into a sterile syringe (or other suitable apparatus). The seed culture was then aseptically injected/introduced into the 7 liters of production culture media.

The seed cultures were incubated for 18 to 48 hours at 35–38° C. and the production cultures were incubated 32 hours (24 to 48) at 35 to 38° C.

Compressed air or oxygen was dispersed throughout the media to create a simmering appearance of the media during the first 8 hours of incubation. Gas flow was increased to give the media the appearance of a low boil from 8 to 24 hours post inoculation. At 18 to 30 hours post inoculation, 50 ml of 1M NaOH was introduced into each production vessel. Gas flow was increased following NaOH addition to give the media the appearance of a rolling boil. Production cultures were allowed to incubate a minimum of an additional 6 to 8 hours prior to inactivation. Preferably, the time from inoculation to harvesting is in the range of 28–36 hours.

The production cultures preferably exhibit dense to extremely dense bacterial growth at the time of inactivation. The production cultures were inactivated with 0.3% to 0.4% v/v formaldehyde following the incubation period.

2. Harvesting Production Cultures

After inactivation, production cultures were allowed to incubate at 35–38° C. for a minimum of 18 hours. Cultures determined to be pure were pooled in large sterile storage vessels and stored at 10–35° C. until further processed. Yield was considered satisfactory upon a spectrophotometer reading of less than or equal to 10% transmission at 540 nm wavelength.

3. Preparation of Product

Following vigorous stirring of the harvest material, a sample shall be collected for standardization. Using a spectrophotometer set at wavelength 540, the % transmission of the sample was determined. Transmissions reading less than 9% were standardized to equal 9% by adding distilled water to the harvest material. Transmissions reading greater than 9% were reworked with material reading less than 9% to achieve a concentration of 10% or less. Prior to standardization, the harvest material was pooled in a sterile mixing vessel and impelled for a minimum of one hour.

A formalin preservative was added to a final product formalin concentration of 0.05–0.2% v/v as measured by the Residual Free Formalin Test. Stabilizer comprising methyl/propyl paraben containing 1–2% red food-grade dye was also added to the final product to a concentration of 1% to 2% v/v. Penicillin was added to the final product to contain 189.250 IU per gallon. Streptomycin can also be added to the final product to contain 250 to 500 mg streptomycin per gallon.

The average serial volume consisted of 400 gallons and the maximum serial shall consisted of 600 gallons. One gallon of the final product +/−5% was dispensed in plastic gallon containers.

The containers can be filled using a pre-chemically sterilized multiple spigot siphon fill/pump system adjusted to deliver one gallon per container. The containers were hand sealed with screw-cap closures. Each gallon contains approximately 20,000 doses.

The product can be used in all poultry at a dosage of about one gallon per 10,000 birds. The appropriate dosage is administered in the drinking water.

The compositions and methods disclosed herein may be advantageously used for all animal species maintained under confinement management conditions including, for example, poultry, pigs, cattle, etc.

From the foregoing detailed description and examples, it will be evident that modification and variations can be made to the products and methods of the invention without departing from the spirit or scope of the invention. Therefore, it is intended that all modifications and variations not departing from the spirit of the invention are within the scope of the claims and their equivalents.

What is claimed is:

1. A vaccine composition comprising in 1 gallon of the composition:

(a) an inactivated *Bordetella avium* or *Ornithobacterium rhinotracheale* bacterin, wherein the bacterin is present in the composition at a concentration permitting a spectrophotometric transmission reading of up to 12% at 540 nm per 10,000 doses; and (b) a preservative;

wherein the peroral administration of the vaccine composition is effective at preventing avian disease.

2. The vaccine composition according to claim 1, wherein the preservative is methyl/propyl paraben.

3. The vaccine composition according to claim 2, wherein the preservative is present in the composition at 1%–2% v/v of composition.

4. The vaccine composition according to claim 1, further comprising an antibiotic.

5. The vaccine composition according to claim 4, wherein the antibiotic is penicillin.

6. The vaccine composition according to claim 1, wherein the transmission reading is up to 5%.

7. The vaccine composition according to claim 1, wherein the transmission reading is about 3.5%.

8. A method for immunizing poultry against avian disease caused by *Bordetella avium* or *Ornithobacterium rhinotracheale*, the method comprising:

(a) mixing one gallon of a vaccine composition comprising (I) an inactivated *Bordetella avium* or *Ornithobacterium rhinotracheale* bacterin, wherein the bacterin is present in the composition at a concentration permitting a spectrophotometric transmission reading of up to 12% at 540 nm per 10,000 doses; (ii) a preservative; and (iii) an amount of water the poultry will consume in about 1–48 hours; and (b) administering the mixed vaccine composition to the poultry for immunization by means of their drinking water.

9. The method according to claim 8, wherein the preservative is methylpropyl paraben.

10. The method according to claim 8, wherein the one gallon of vaccine composition is mixed with the amount of water the poultry will consume in about 24 hours.

11. The method according to claim 8, wherein the vaccine further comprises an antibiotic.

12. The method according to claim 11, wherein the antibiotic is penicillin.

13. The method according to claim 8, wherein the transmission reading is up to 5%.

14. The method according to claim 8, wherein the transmission reading is about 3.5%.

15. The method according to claim 9, wherein the preservative is present in the composition at 1%–2% v/v of composition.

* * * * *